(12) United States Patent
Lindqvist et al.

(10) Patent No.: US 10,660,906 B2
(45) Date of Patent: May 26, 2020

(54) HYALURONAN CONJUGATES WITH PHARMACEUTICALLY ACTIVE SUBSTANCES, METHODS AND COMPOSITIONS

(71) Applicant: SYNARTRO AB, Uppsala (SE)

(72) Inventors: Bengt Lindqvist, Uppsala (SE); Rune Ringom, Uppsala (SE)

(73) Assignee: SYNARTRO AB, Uppsala (SE)

( * ) Notice: Subject to any disclaimer, the term of this patent is extended or adjusted under 35 U.S.C. 154(b) by 5 days.

(21) Appl. No.: 15/121,675

(22) PCT Filed: Feb. 21, 2015

(86) PCT No.: PCT/IB2015/051331
§ 371 (c)(1),
(2) Date: Aug. 25, 2016

(87) PCT Pub. No.: WO2015/128787
PCT Pub. Date: Sep. 3, 2015

(65) Prior Publication Data
US 2016/0367684 A1  Dec. 22, 2016

Related U.S. Application Data

(60) Provisional application No. 61/945,491, filed on Feb. 27, 2014.

(51) Int. Cl.
| A61K 47/48 | (2006.01) |
| A61K 31/573 | (2006.01) |
| A61K 31/196 | (2006.01) |
| A61K 47/61 | (2017.01) |

(52) U.S. Cl.
CPC .......... *A61K 31/573* (2013.01); *A61K 31/196* (2013.01); *A61K 47/61* (2017.08)

(58) Field of Classification Search
CPC .... A61K 31/196; A61K 31/573; A61K 47/61; A61K 47/4823
USPC ......................................................... 514/54
See application file for complete search history.

(56) References Cited

U.S. PATENT DOCUMENTS

| 4,716,154 A | 12/1987 | Malson et al. |
| 7,202,230 B2 * | 4/2007 | Rivarossa ............ A61L 31/041 424/486 |
| 2011/0083991 A1 * | 4/2011 | Miyamoto ........... A61K 31/192 206/571 |

FOREIGN PATENT DOCUMENTS

| EP | 1710257 A1 | 10/2006 | |
| WO | 96/35720 A1 | 11/1996 | |
| WO | 96/35721 A1 | 11/1996 | |
| WO | 2007/126154 A1 | 11/2007 | |
| WO | 2009/074678 A2 | 6/2009 | |
| WO | WO 2009/074678 A2 * | 6/2009 | ............ A61K 47/48 |
| WO | WO2009/074678 A2 * | 6/2009 | ............ A61K 47/48 |
| WO | WO 2013/053856 A1 * | 4/2013 | ............... A61K 9/00 |
| WO | 2014/122431 A1 | 8/2014 | |

OTHER PUBLICATIONS

Trisha Gura's, Science, Nov. 1997, 279(5340), 1041-42.*
L Stefan Lohmander et al., Intra-articular hyaluronan injections in the treatment of osteoarthritis of the knee: a randomised, double blind, placebo controlled multicentre trial, Annals of the Rheumatic Diseases ; 55: 424-431 (1996).
Dong et al, Journal of Applied Polymer Science, 130(2):927-932 (Apr. 11, 2013).
Song et al, Pharmaceutical Research, May 20, 2014, pp. 240-246. (cited as Xu et al in the International Search Report).

* cited by examiner

*Primary Examiner* — Ganapathy Krishnan
(74) *Attorney, Agent, or Firm* — Biospark Intellectual Property Law

(57) ABSTRACT

A method for manufacturing a hyaluronan conjugate comprises providing hyaluronan in solution or gel form, reacting the hyaluronan in solution or gel form with anhydride reagent to provide a hyaluronan hemi-ester with a chain of length L between the hyaluronan and the ester group, and subsequently binding the hyaluronan hemi-ester to a pharmaceutically active compound. A hyaluronan conjugate comprises hyaluronan having free hemi-ester-groups and a pharmaceutically active compound bound to the hyaluronan via hemi-ester groups, wherein the hemi-ester groups have a chain length of 2-9 atoms. The hyaluronan conjugate is suitable for use in various methods of treatment in human or veterinary medicine and for preparation of a medicament for use in human or veterinary medicine.

18 Claims, 1 Drawing Sheet

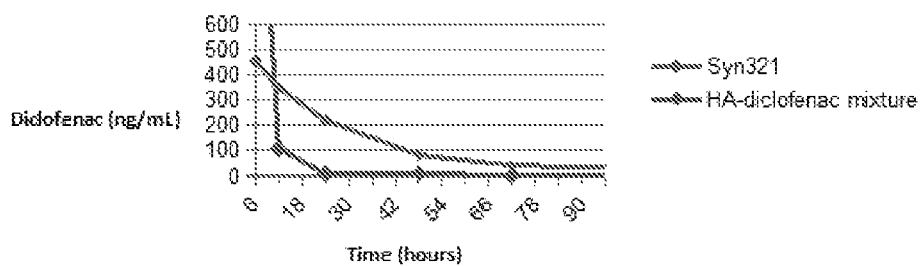

HYALURONAN CONJUGATES WITH PHARMACEUTICALLY ACTIVE SUBSTANCES, METHODS AND COMPOSITIONS

FIELD OF THE INVENTION

The present invention relates to hyaluronan conjugates comprising hyaluronan having free hemi-ester-groups and a pharmaceutically active compound bound to the hyaluronan via hemi-ester groups. The hyaluronan conjugates are suitable for use in various methods of treatment in human or veterinary medicine and for preparation of a medicament for use in human or veterinary medicine. The invention also relates to methods for manufacturing hyaluronan conjugates and compositions comprising hyaluronan conjugates.

BACKGROUND OF THE INVENTION

Hyaluronan is an anionic, nonsulfated glycosaminoglycan distributed throughout connective, epithelial, and neural tissues. Hyaluronan is a polysaccharide built of disaccharide repeating residues of -3)-N-acetyl-β-D-glucose amine-(1-4)-β-D-glucuronic acid-(1-., provided as a sodium salt:

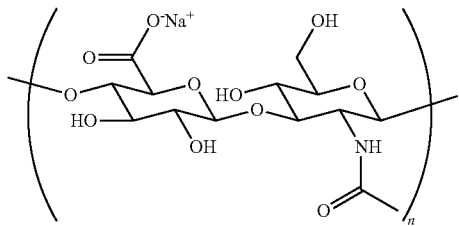

It is a very large molecule and can have a molecular weight of several or more million Daltons. Hyaluronan is present in most tissues in mammals in the extracellular matrix. In mammals, hyaluronan is found in higher amounts in the umbilical cord, and it is a constituent of the vitreous body and joint cartilage. Hyaluronan is an important constituent of the synovial fluid. It has high viscosity and provides lubrication to the joints.

Hyaluronan and modified derivatives of hyaluronan are currently used in in vivo applications such as eye surgery, cosmetic injections and intraarticular injections to treat osteoarthritis.

Osteoarthritis is a degenerative joint disease and a very common condition. Knee joints, hip joints and shoulder joints are often affected, and symptoms can be disabling to different degrees. A common treatment is oral intake of non-steroidal anti-inflammatory drugs (NSAIDs). Some of these NSAIDs are known to give gastrointestinal problems after extended use and such intestinal complications are far from uncommon. In osteoarthritis, local administration of the drug, e.g. by injection, would be desirable, but the duration of a small NSAID molecule is relatively short and a more prolonged duration is necessary for efficient treatment.

Many studies have been performed to investigate the efficiency of hyaluronan in arthritis treatment, see Lohmander et al (1996) [1], but the results of various studies have been contradictory and lately some reports indicate that injection of hyaluronan is not efficient, see Jorgensen et al [2] and Arrich et al [3]. In spite of this, several hyaluronan products for treatment of osteoarthritis are currently in use.

In the ophthalmic area, cataract surgery is quite common and typically steroid-containing eye-drops are used post-surgery to suppress inflammation. The patients are often elderly and sometimes have difficulties taking the eye drops as prescribed. A slow release composition that could be left in the eye could alleviate the use of such inflammation suppressing eye-drops.

There has been a considerable interest in controlled release systems for the distribution of active pharmaceuticals over an extended time period, and hyaluronan has been used both in mixtures with drugs and in systems where a drug is attached to the hyaluronan molecule, for example, with a covalent bond, usually with an ester or amide group, directly or through a spacer molecule.

EP1710257 A1 discloses a drug bound with an ester linkage to a spacer which in turn is linked through an amide bond to hyaluronan. The drug is released by cleavage of the ester bond, leaving the amide residue on the hyaluronan polymer. An amine is first made at position C-6 of the GlcNAc moiety and then coupling is made through an amide linkage through to hyaluronan.

WO 96/35720 and WO 96/35721 disclose succinyl hemi-ester derivatives of drugs. In WO 96/35721, the derivatives are synthesized by a method wherein, inter alia, the carboxyl group of the hemi-ester is converted to a reactive acid chloride using oxalyl chloride, and the drug-hemi-ester-chloride is subsequently reacted with hyaluronan in DMF and an excess of pyridine to obtain an ester bond to hyaluronan or hyaluronan benzyl ester. Because succinic hemiesters are made of pharmaceutically active compounds, and then acid chlorides are made from the drug-hemiesters, the pharmaceutically active compound must not be susceptible to chlorination at other positions. The derivatized drugs are then reacted with hyaluronan in an aprotic solvent. In order to dissolve hyaluronan in an aprotic solvent, the hyaluronan must be modified to a hydrophobic salt such as tetraalkyl ammonium or tetraalkyl phosphonium, or to make some other hydrophobic derivative, for example, esters. WO 96/35721 references Kyyronen et al [7], where the release of methylprednisolone from microspheres and films made of ethyl esters or benzyl esters of hyaluronan and of the methylprednisolone ester linked to hyaluronan was studied in vitro and in vivo. In the in vivo model, the ocular bioavailability was studied by measuring the drug released into tear fluid. Hemi-succinate esters of hyaluronan are described in WO 96/35720 with the purpose to make various heavy metal salts of the polymer.

WO 2009/074678 describes the coupling of camptothecin to hyaluronan via a linker. The procedure involves the synthesis of camptothecin hemi-succinate, followed by the activation of the carboxyl of the hemi-succinate to the n-hydroxy succinimide ester, which in turn is reacted with the tetrabutylammonium salt of hyaluronan in dimethyl sulfoxide. Also a camptothecin-(aminoacid or peptide)-NH—CO—CH$_2$—CH$_2$—CO-hyaluronan derivative is described. The procedure is similar to that used in WO 96/35721, and requires that a hydrophobic salt of hyaluronan is made before the coupling reaction to hyaluronan.

In the described publications, a hemi succinate ester of the drug is made first and then reacted with hyaluronan. Easier methods for production of hyaluronan conjugates are desired, as are hyaluronan conjugates having improved properties.

SUMMARY OF THE INVENTION

Accordingly, it is an object of the invention to provide hyaluronan conjugates, improved methods for production of hyaluronan conjugates, and compositions comprising hyaluronan conjugates.

In one embodiment, the invention is directed to methods for manufacturing a hyaluronan conjugate. The methods comprise providing hyaluronan in solution or gel form, reacting the hyaluronan in solution or gel form with anhydride reagent to provide a hyaluronan hemi-ester with a chain of length L between the hyaluronan and the ester group, and subsequently binding the hyaluronan hemi-ester to a pharmaceutically active compound.

In another embodiment, the invention is directed to hyaluronan conjugates comprising hyaluronan having free hemi-ester-groups and a pharmaceutically active compound bound to the hyaluronan via hemi-ester groups, wherein the hemi-ester groups have a chain length of 2-9 atoms.

In additional embodiments, the invention is directed to compositions comprising the hyaluronan conjugates and methods of treatment using the hyaluronan conjugates. In yet additional embodiments, the invention is directed to use of a hyaluronan conjugates for preparation of a medicament for use in human or veterinary medicine.

The hyaluronan conjugates covalently bind the pharmaceutically active substance and allow controlled in vivo release by enzymatic degradation of ester bonds. Additional advantages and improvements of the conjugates, methods and compositions of the invention will be apparent in view of the detailed description.

BRIEF DESCRIPTION OF THE DRAWING

The FIGURE shows a comparison of the pharmacokinetic effects of a hyaluronic conjugate according to the invention as compared with a hyaluronan drug mixture upon injection as described in Example 13

DETAILED DESCRIPTION

The hyaluronan conjugates comprise hyaluronan having free hemi-ester-groups and a pharmaceutically active compound bound to the hyaluronan via hemi-ester groups, wherein the hemi-ester groups have a chain length L of 2-9 atoms. Thus, in the hyaluronan conjugate, some of the hemi-ester-groups are free and some of the hemi-ester-groups are bound to the pharmaceutically active compound. In a specific embodiment, the hyaluronan conjugates are manufactured by providing hyaluronan in solution or gel form, reacting the hyaluronan in solution or gel form with an anhydride reagent to provide a hyaluronan hemi-ester with a chain of length L between the hyaluronan and the ester group, referred to herein as activated hyaluronan, and subsequently binding the hyaluronan hemi-ester to a pharmaceutically active compound.

According to a specific embodiment of the invention, the hemi ester chain comprises a carbon backbone, optionally including one or two oxygen atoms in the backbone. The carbon backbone of the hemi ester chain can optionally include one or more branches of alkyl, aryl, oxy-alkyl or oxy-aryl.

In a more specific embodiment, the chain that is bound to the hyaluronan is of the formula:
—C(O)—(CHR)$_n$—(CH$_2$)$_{(m-n)}$—COO—, where n is 0 or 1, m=2-8, e.g. 2, 3, 4, 5, 6, 7 or 8, and R is alkyl, aryl, O-alkyl or O-aryl, or
—C(O)—(CHR)$_2$—(CH$_2$)$_{(p-1)}$—O—(CH$_2$)$_q$—COO—,
where n is 0 or 1, p and q are individually 1-4, e.g. 1, 2, 3 or 4, and R is alkyl, aryl, O-alkyl or O-aryl.

In further embodiments, the chain that is bound to the hyaluronan is of the formula:

—C(O)—(CH$_2$)$_m$—COO—, where m=2-8, e.g. 2, 3, 4, 5, 6, 7 or 8,
—C(O)—(CH$_2$)$_p$—O—(CH$_2$)$_q$ COO— where p and q are individually 1-4, e.g. 1, 2, 3 or 4, or
—C(O)—(CH$_2$)$_r$—O—(CH$_2$)$_s$—O—(CH$_2$)$_t$—COO—
where r and t are individually 1-2 and s is 2.

One skilled in the art will appreciate that in the reaction of the hyaluronan with an anhydride reagent, the activated intermediate includes free hemiester groups which may be in the form of salts, e.g., sodium salts, of the ester groups, wherein, in each of the above formulas, —COO— is —COONa.

According to another aspect of the invention the hyaluronan is cross linked to form a gel, for example as disclosed in Laurent et al [4] and Maïson et al [5], which are incorporated herein by reference, before activation by the formation of the hemi-ester and/or subsequent binding of a drug via ester or amide binding, as further illustrated in Examples 16-19.

Various aspects of the invention in the following are illustrated by the formation of hyaluronan-succinyl-hemi-esters (HSE) and subsequent binding of pharmaceutically active substances by ester binding. Anhydrides other than succinic anhydride, and esters formed therefrom, and within the scope of the invention are equally suitable for use in the various specific embodiments of the invention described herein. In one specific embodiment, glutaryl-hemi esters are employed. Analogous methods for introducing chains of other lengths, as disclosed above, will be apparent to one skilled in the art in view of the present disclosure.

The invention provides hyaluronan conjugates in which the action of esterase enzymes results in controlled release of well-defined degradation products comprising hyaluronan, without substituents, and a pharmaceutically active substance, without substituents.

According to a specific embodiment of the invention, a hyaluronan-succinyl-hemi-ester with a high degree of purity is provided. A product like hyaluronan derived from natural sources very often contains contaminants in low amounts. A hyaluronan product (Healon®) used in eye surgery has been on the market for many years and is produced according to a very complicated method. Without being bound by theory, the anhydride reaction, for example the succinylation reaction, according to the present invention may result in modifications also of contaminating proteins via their amino groups to make them less immunogenic or allergic. For example, succinylated gelatin is a well-known ingredient in infusion solutions and is apparently well tolerated (in Sweden, marketed by B. Braun, Melsungen Germany, under the name Gelofusine).

In a specific embodiment of the manufacturing method of the invention, the hyaluronan in solution or gel form is reacted with an anhydride reagent, e.g. succinic anhydride. A solution of the hyaluronan may be provided using a suitable solvent for solid sodium hyaluronate, e.g. formamide, with the addition of a tertiary amine, e.g pyridine or a substituted pyridine. In a specific embodiment, the solvent is pyridine, optionally with the addition of 4-dimethyl-amino-pyridine (DMAP) or 2,6-dimethyl-4-dimethylamino-pyridine. This procedure allows for dissolution of the solid sodium hyaluronate without extra steps such as ion exchange to the acid form, hyaluronic acid, typically used in the prior art.

That is, in previously described methods referred to above, for example WO 96/35720, dimethyl formamide (DMF) is used as a solvent. In this solvent, however, sodium hyaluronate is not soluble, and an ion exchange to the acid form of hyaluronan in water or transfer to an amine salt is required before dissolution in DMF, followed by evaporation to remove water, re-dissolution in DMF and then addition of reagents.

The procedure according to the present method allows the addition of reagents directly after dissolution in the formamide solvent, thus giving a simpler and shorter procedure than those commonly employed in the prior art for the synthesis of the hemi-ester of Formula I:

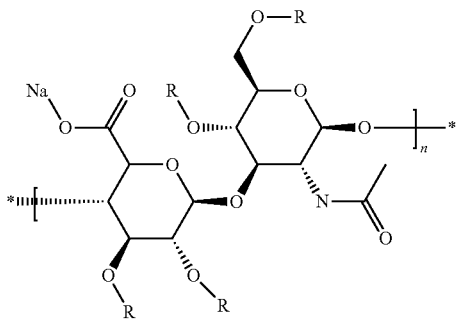
(I)

in which R is H or the ester chain, for example, —CO—CH$_2$—CH$_2$—CO—O—Na in the case of succinyl anhydride.

The degree of ester substitution can be influenced by changing the proportion of the anhydride reagent to the hyaluronan polymer, the reaction time, and the temperature.

Typically, without raising the temperature above room temperature, an average degree of substitution (DS) of up to 3 moles of hemi-succinate per mole hyaluronan repeating disaccharide unit can be obtained. In a specific embodiment, the average degree of substitution is 0.5 to 3 and, in a more specific embodiment, is 1-3 or 2-3 mol hemi-ester, e.g. hemi-succinate, per mol hyaluronan repeating disaccharide unit.

The hemi-ester, e.g. succinylated hyaluronan (HSE), can then be reacted with amino group-containing compounds to obtain amides on the carboxyl groups which are exposed on the succinyl-hyaluronan. A desired pharmaceutically active agent can be provided with an amino functionality in accordance with a procedure described herein. In specific embodiments, the amino functionality is combined with a longer moiety in order to space the pharmaceutically active agent from the hyaluronan and provide better access for the degrading enzymes in vivo. Additionally, in specific embodiments, coupling of the amine-functionalized pharmaceutically active agent to the hyaluronan hemi-ester group may be performed in water-containing media, i.e., water or an aqueous solvent, for example in a DMF-water mixture or in suitable water-based buffers. This feature makes it possible to link molecules that are difficult to dissolve in aprotic solvents.

An example of such a pharmaceutically acceptable compound containing an amino-group is [2-(2,6-dichloro-phenylamino)-phenyl]-acetic acid 2-(2-amino-ethoxy)-ethyl ester of Formula (II), which can be obtained as described in Examples 1 and 2 from diclofenac:

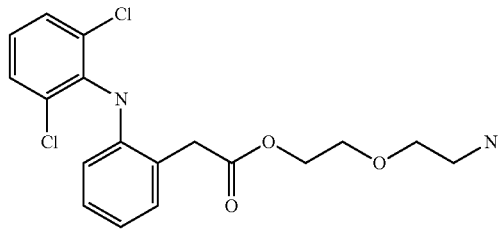
(II)

The 2-(2-amino-ethoxy)-ethyl ester moiety is advantageous as the diclofenac substituent is spaced from the hyaluronan polymer backbone and may advantageously provide easier access to the ester moiety for degrading enzymes in the synovial fluid or other body fluids, depending on the application.

Formula (III) shows a schematic representation of a resulting HSE-drug conjugate:

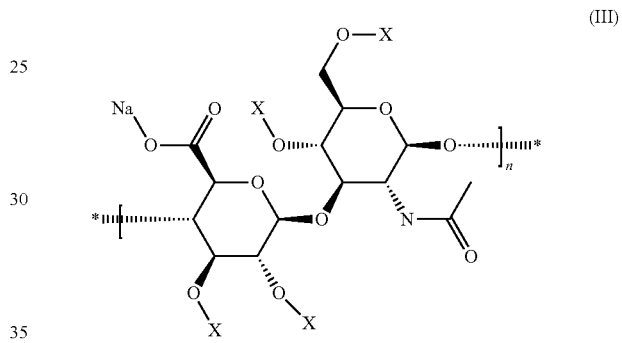
(III)

wherein X is H, —CO—CH$_2$CH$_2$—COONa, —CO—CH$_2$CH$_2$—CO—NH—CH$_2$CH$_2$—O—CH$_2$CH$_2$—O-DRUG, or —CO—CH$_2$CH$_2$—CO—NH—CH$_2$CH$_2$—O—CH$_2$CH$_2$—O—CO—CH$_2$CH$_2$—CO-DRUG, wherein DRUG represents the pharmaceutically active compound.

In theory, the drug molecules can occupy all carboxyl groups exposed by the HSE, but in practice, higher substitutions can unfavorably change the properties of the polymer, particularly if a solution suitable for injection is desired. For the substitution with diclofenac, an average degree of substitution (DS) less than or equal to 0.3 mols of drug per mol hyaluronan disaccharide repeating unit is favorable for the formulation of an injectable solution. Depending on the intended use, an average substitution degree from 0.01 to 0.3, in particular 0.05 to 0.2, mol drug per mol hyaluronan disaccharide repeating unit may be employed. For drugs other than diclofenac, other substitution degrees might be preferred. For the manufacture of solid formulations, for example, films or particles, the intended use will determine the preferred DS, and for applications where high doses are needed, an average DS up to 3 mols drug per mol hyaluronan is preferred.

In another specific embodiment of the invention, a steroid such as dexamethasone is linked to succinyl-hyaluronan. For example, the dexamethasone derivative O1-[2-(2-aminoethoxy)ethyl] O4-[2-[(8S,9R,10S,11S,13S,14S,16R,17R)-9-fluoro-11,17-dihydroxy-10,13,16-trimethyl-3-oxo-6,7,8,11,12,14,15,16-octahydrocyclopenta[a]phenanthren-17-yl]-2-oxo-ethyl] butanedioate described in Example 9 and shown by Formula (IV) may be used for reaction with the succinyl-hyaluronan hemi-ester:

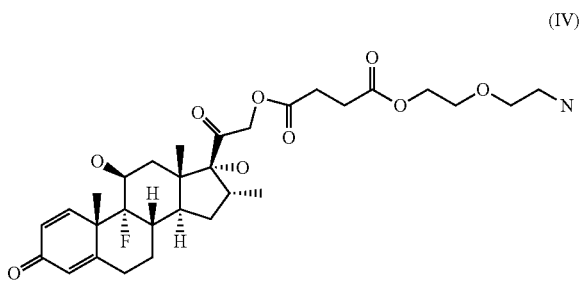

(IV)

The procedure for the coupling of the molecule to succinyl hyaluronan is described in Example 10.

This dexamethasone-hyaluronan, HSE-dexamethasone conjugate can be dissolved in physiological saline buffered to pH 7.2, and heat sterilized as described above without any substantial release of drug molecule.

The HSE-dexamethasone can be used to prevent complications, i.e., inflammation, after cataract surgery. In a specific embodiment, 20 to 100 µL of a 0.5 to 2% solution of HSE-dexamethasone in physiological saline is left in the anterior chamber after cataract surgery, eliminating the risk for inflammatory reactions after cataract surgery. Currently, dexamethasone-eye drops are routinely prescribed after cataract surgery and typically for administration 3-4 times per day. The patients are often elderly and have difficulties using the eye drops as prescribed. Leaving a small amount of HSE-dexamethasone in the anterior chamber after cataract surgery will make the eye drops unnecessary, the surgery more safe and a positive outcome more likely.

Yet another embodiment of the hyaluronan conjugate of the invention includes an anticancer drug such as a chemotherapeutic drug as an aid in the treatment of cancer. In one embodiment, the conjugate can be left locally at a site of surgery to prevent the growth of residual cancer cells. For example, in one embodiment, cisplatin is reacted with HSE, resulting in a HSE-cisplatin-conjugate of Formula V for use in cancer therapy

(V)

Other pharmaceutically active compounds suitable to link to a hyaluronan hemi-ester, e.g. HSE, with the chemistry described herein include, for example, but are not limited to, ibuprofen, ketoprofen, naproxen, bromfenac, aceclofenac, prednisolone, metronidazole podophyllotoxin, paclitaxel, docetaxel, doxorubicin, daunorubicin, adapalene, azithromycin, levofloxacin, aciclovir, cyclosporine, tacrolimus, latanoprost, cromoglicic acid, levocabastine, nedocromil, olopatadine, bepotastine and morphine. Some drugs are hydrophobic and thus have a poor solubility in water solutions. Linking those drugs to a hyaluronan matrix according to the present invention, e.g. highly hydrophilic hyaluronan-succinyl-ester, gives higher solubility in water solutions, and facilitates the ability to provide pharmaceutical formulations containing such drugs.

The hyaluronan conjugate can be provided in various physical forms. The product can be made in different physical forms and shapes, both as solutions and solids, and be sterilized, e.g. by autoclavation. In one embodiment, the hyaluronan is provided as a solution with a concentration, for example, of 1 to 40 mg/mL, more specifically, 10-20 mg/mL, in a physiologically acceptable liquid, for example, in buffered physiological saline, suitably at a pH 6.5-7.5. The solution can be heat sterilized at 121° C. for 15 minutes ($F_0 15$) or at 128° C. corresponding to $F_0 13$ as describe by Remington [8] (see Example 7), and supplied in vials or in ready to use syringes. The hyaluronan conjugate is surprisingly stable during heat sterilization, as shown in the Examples, and less than 1% of the covalently bound drug was released during sterilization.

According to a further aspect of the invention, a pharmaceutical formulation with controlled rheology within a wide range is provided. A solution of the hyaluronan conjugate as described above may be mixed with non-conjugated hyaluronan. In a specific embodiment, the hyaluronan conjugate is mixed with non-conjugated hyaluronan. In a specific embodiment, the non-conjugated hyaluronan has a molecular weight from about 100,000 to about 4,000,000 Da. In further embodiments, a solution of the hyaluronan conjugate and non-conjugated hyaluronan comprises the conjugated hyaluronan, for example, in concentrations of about 01. to 10 weight %, or, more specifically, up to about 3 weight %, of the final formulation.

In additional embodiments, solutions of the hyaluronan conjugate can be evaporated to make dry films or processed to dry particles of various sizes, which can be used in surgery as implants or topically as dressings to supply active pharmaceuticals, e.g. incorporated in carrier matrices, depending on the intended use. The hyaluronan conjugate can also be used to cover part of the eye to deliver drug to the eye.

The hyaluronan conjugate may also be made into sponges, beads, rods or other constructs adopted for a given application, e.g. to be placed under the eyelid for sustained release drug delivery. It can also be left inside the eye, or in any other suitable compartment of the body, after surgery.

Gels, made in accordance with Mälson et al [5], can be employed in the hyaluronan conjugate. One procedure to achieve this is described in Example 11.

Further aspects of the invention comprise use of the hyaluronan conjugates in human or veterinary medicine. The invention provides excellent tools for delivery of pharmaceutically active drug for treatment of various conditions in humans as well as in animals, e.g. to treat osteoarthritis in man or animals (e.g. horses), in cataract surgery to reduce inflammation, or to treat various cancers, just to mention a couple of applications. The hyaluronan conjugates will be delivered in amounts sufficient to provide a respective pharmaceutically active agent in an amount known to provide a desired therapeutic effect.

The following examples are provided to further illustrate various embodiments of the invention and demonstrate conjugates of soluble hyaluronan-succinyl hemi-esters in solution or gel form with active pharmaceutical agents, as well as their use in therapy.

Example 1

[2-(2,6-Dichloro-phenylamino)-phenyl]-acetic acid 2-(2-tert-butoxycarbonylamino-ethoxy)-ethyl Ester Diclofenac (1.2 g), [2-(2-Hydroxy-ethoxy)-ethyl]-carbamic acid tert-butyl ester (1.4 g) and 4-dimethylaminopyridine (DMAP) (76 mg) were dissolved in dichloromethane (DCM) (6 mL). The reaction mixture was cooled on an ice-water bath, 1-ethyl-3-(3-dimethylaminopropyl)carbodiimide (EDC) (1.31 g) was added and was stirred for 4 h while the ice was melting. LCMS of the reaction mixture showed that the expected product was formed and no starting material was left. The reaction mixture was transferred to a separation funnel and about 7 mL of DCM was added. The DCM phase was washed with water (~3*10 mL) and the DCM phase was evaporated. Obtained 2 g crude material. Flash chromatography in EtOAc/Heptane 1/1 gave 1.166 g, 95% pure LCMS Example 2

2-(2,6-Dichloro-phenylamino)-phenyl]-acetic acid 2-(2-amino-ethoxy)-ethyl Ester

[2-(2,6-Dichloro-phenylamino)-phenyl]-acetic acid 2-(2-tert-butoxycarbonylamino-ethoxy)-ethyl ester (1166 mg) from Example 1 was dissolved in DCM (9 mL). Trifluoroacetic acid (TFA) (1 mL) was added. The reaction mixture was heated at 40° C. for 15'. 2-(2,6-Dichloro-phenylamino)-phenyl]-acetic acid 2-(2-amino-ethoxy)-ethyl ester was obtained after evaporation as the di-trifluoro-acetate, 1.47 g.

Example 3

Hyaluronan-succinyl-ester (HSE)

Sodium hyaluronate (1000 mg) was dissolved in formamide (100 mL). Pyridine (2014 µL), DMAP (30 mg) and succinic anhydride (2494 mg) were added. The reaction mixture was stirred at room temperature. The reaction mixture was dialyzed in water for 24 hours. The reaction mixture was dialyzed in 1% NaCl, for 24 hours. The product was precipitated in ethanol 1 L, collected and dried in vacuum overnight. HSE was obtained 1.043 g, DS 2.3 (1 HNMR)

Example 4

HSE-Diclofenac

Hyaluronan-succinyl-ester (HSE) from Example 3, (400 mg) was dissolved in water (10 mL). Dimethyformamide (DMF) (30 mL) was added and the solution was stirred until a homogeneous solution was obtained. N-methylmorpholine (27.3 µL) and 1-hydroxybenzotriazole (HOBT) (2 mg) were added and mixed well in the solution before the addition of a DMF-solution of 2-(2,6-Dichloro-phenylamino)-phenyl]-acetic acid 2-(2-amino-ethoxy)-ethyl ester. 297 mg/mL (249 µL, 74 mg) from Example 2. The solution was mixed well. EDC (24 mg) was added and mixed in the solution. The solution was left overnight at room temperature. NaCl saturated water solution (1.1 mL) was added and mixed in the reaction mixture. The viscous solution was slowly poured into stirred ethanol (120 mL). The product precipitated and was left for 2 h. The precipitate was filtered off washed with ethanol and dissolved in phys phosphate-NaCl buffer (40 mL). The solution was filtered through a glass filter pore 3. The filtered solution was transferred to a beaker. Ethanol (150 mL) was slowly added, and the precipitate was left in the ethanol overnight. The precipitate was collected and washed with ethanol and acetone. The collected product was dried in vacuum for 2 h. Obtained 237.9 mg. DS 0.04 according to proton NMR.

Example 5

HSE-Diclofenac

HSE (400 mg) was dissolved in water (10 mL) in a 50 ml syringe connected to another syringe of the same size. DMF (30 mL) was added, and the solution was pushed back and forth for at least 15 times, until the solution appeared homogeneous. N-methyl-morpholine (68.2 mL) and HOBT (4 mg) were added and well mixed in the DMF-water solution. The 2-(2,6-Dichloro-phenylamino)-phenyl]-acetic acid 2-(2-amino-ethoxy)-ethyl ester (190 mg) was added as a DMF (296 mg/mL) solution. The solution was mixed well, before the addition of EDC (60 mg). The reaction mixture mixed by pushing the viscous solution back and forth at least 15 times. The reaction was left at room temperature overnight. The product was precipitated in ethanol (150 mL) The precipitate was left in the ethanol for a few hours. The precipitate was collected and squeezed to minimize residual ethanol. The precipitate was dissolved in physiological NaCl phosphate buffer (40 mL), using the two syringe setup. It was left overnight. The product was precipitated in ethanol (150 mL), and left to mature for a few hours. The precipitate was collected, washed with ethanol. The precipitate was squeezed to get rid of some ethanol, and then added to phys. NaCl buffer (40 mL) and stirred overnight. Ethanol (150 mL) was added and the product precipitated. The precipitate was left to mature overnight. The precipitate was collected and washed with ethanol three times, and with acetone three times, and dried in vacuum overnight. Obtained 358 mg. The DS=0.15 calculated from proton NMR.

Example 6

HSE-Diclofenac

HSE according to Example 3 (200 mg) was dissolved in water (5 mL). DMF (15 mL) was added to obtain a solution of succinyl hyaluronan in water/DMF, 1/3 (20 mL). N-methyl-morpholine (33 µL), HOBT (0.5 mg) and a DMF solution of 2-(2,6-Dichloro-phenylamino)-phenyl]-acetic acid 2-(2-amino-ethoxy)-ethyl ester 397 mg/mL (46.4 µL, 18.4 mg) were added to the stirred succinyl-hyaluronan solution. EDC (5.8 mg) was added. The reaction mixture was mixed thoroughly and left over night at room temperature. Sodium chloride (200 mg) was added as a sat solution (359 mg/mL) to the DMF-water solution. The product was precipitated in ethanol (100 ml) and stirred for 2.5 h. The precipitate was collected and dissolved in 1% NaCl (20 mL) and precipitated in ethanol (80 mL). The solid material was collected, and once more dissolved in 1% NaCl and precipitated. The precipitate was dissolved in water and lyophilized. Obtained 177 mg. According to proton NMR the degree of substitution is 0.22.

Example 7

HSE-Diclofenac Sterile Formulation

Diclofenac-substituted hyaluronan was dissolved in a physiological sodium chloride phosphate buffer pH 7.4 to a concentration of 10 mg/mL and filled in 2 mL syringes. The syringes were heat sterilized with a method corresponding to $F_0$ 13.

$F_0$ means the equivalent amount of time, in minutes at 121.1° C., which has been delivered to a product by the sterilization process. For a calculation, a z value of 10° C. is assumed; the term z value means the slope of the thermal death time curve and may be expressed as the number of degrees required to bring about a tenfold change in the death rate. In practice, the knowledge of the temperature values as the continuous function of elapsing time is not available, and $F_0$ is calculated as:

$$F_0 = \Delta t \Sigma 10^{\frac{T-121.1}{s}}$$

where $\Delta t$ is the time interval between two consecutive measurements of T, T is the temperature of the sterilized product at time t, and z is the temperature coefficient assumed to be equal to 10.

After the heat treatment, one of the syringes was analyzed for diclofenac released. The syringe was emptied into acetonitrile which makes the derivatized hyaluronan precipitate. The precipitate was removed and the solution was analyzed on LCMS. The release of diclofenac from the heat sterilized product was found to be less than 1%.

Example 8

O4-[2-[2-(tert-butoxycarbonylamino)ethoxy]ethyl] O1-[2-[(8S,9R,10S,11S,13S,14S,16R,17R)-9-fluoro-11,17-dihydroxy-10,13,16-trimethyl-3-oxo-6,7,8,11,12,14,15,16-octahydrocyclopenta[a]phenanthren-17-yl]-2-oxo-ethyl] Butanedioate Dexamethasone (200 mg), succinic acid mono-[2-(2-tert-butoxycarbonylamino-ethoxy)-ethyl] ester (171 mg, 1710 µL), added as a solution in DCM (100 mg/mL) and DMAP (7 mg) are mixed in DCM (3 mL). The mixture is cooled on an ice bath before the addition of EDC (108 mg). The mixture was stirred over night while the ice water bath was melting. Over night a clear solution was obtained. DCM (3 mL) was added to the reaction mixture. And the reaction mixture was washed with water (3×5 mL). The DCM phase was collected and dried with Mg SO4 and evaporated. Obtained 288 mg.

Example 9

O1-[2-(2-aminoethoxy)ethyl] O4-[2-[(8S,9R,10S,11S,13S,14S,16R,17R)-9-fluoro-11,17-dihydroxy-10,13,16-trimethyl-3-oxo-6,7,8,11,12,14,15,16-octahydrocyclopenta[a]phenanthren-17-yl]-2-oxo-ethyl] Butanedioate Dexamethasone with boc-protected spacer from Example 8 (288 mg) was dissolved in DCM (5 mL), and TFA (0.5 mL) was added. The solution is left over night at room temperature. LCMS shows that protection group is removed. The reaction mixture was evaporated and dried in vacuum. Obtained 402 mg of the product (Dexamethasone with spacer) as a TFA-salt.

Example 10

HSE-Dexamethasone

Succinyl hyaluronan (400 mg) was dissolved in water (10 mL), DMF (30 mL) was added. The mixture was stirred overnight. To the cooled solution (ice-water bath) were added HOBT (3 mg), N-methylmorpholine (45 µL) and dexamethasone with the spacer from Example 9 (167 mg). The viscous solution was stirred for a few minutes and then EDC (40 mg) was added. The solution was left over night at room temperature. NaCl (sat) (1.1 mL) was added and stirred for a few minutes. Ethanol (400 mL) was added in portions, the first two 50 mL portions were used to transfer the viscous material to a beaker. The precipitate was stirred for 3 h in the ethanol. The precipitate was collected on a glass filter. The precipitate was dissolved stirring overnight in water (40 mL). Saturated NaCl (1.1 mL) was added. The mixture was stirred for 10 min and the product was precipitated in ethanol (400 mL), collected on a glass filter, and washed in acetone (4×50 mL). Drying in vacuum over several days gave 350 mg. $^1$H NMR, indicates that the degree of substitution is about 0.07, i.e., about 7 dexamethasone units per 100 disaccharide repeating units.

Example 11

Preparation of Succinylated HA-Gel (HSE-Gel)

Dried HA gel particles (100 mg) were shaken in formamide (10 mL) for 20 hours to give a swollen gel. Succinic anhydride was dissolved in formamide (2 mL) and added. The round bottomed flask was shaken manually for 5 minutes before DMAP (3.2 mg in pyridine 201 µL) was added. The reaction mixture was shaken for 24 hours and 250 µL of a saturated NaCl was added followed by 36 mL of absolute ethanol. The precipitate was allowed to mature for 3 hours. The precipitate was collected by suction filtration and the white powder obtained was washed with ethanol (2×2 mL). To the white powder was added physiological saline buffer pH 7.2 (10 mL) and the gel was allowed to swell for 1 hour. Absolute EtOH (30 mL) was added while stirring. The mixture was shaken for 24 hours. The white powder was collected and washed with EtOH (2×2 mL) and acetone (2 mL) and dried in vacuo. Yield: 80 mg.

Example 12

HSE-Gel with Dexamethasone Substituents

HSE-gel 40 mg (Example 11) was swollen in water (2 mL). DMF (6 mL) was added and the solution was shaken overnight. Dexamethasone with spacer (Example 9) (170 µL of a solution containing 100 mg/mL in DMF), N-methylmorpholine (8 µL) and HOBT (1 mg) was added and the mixture was shaken for 30 minutes before EDC (8 mg) was added. The reaction mixture was shaken at room temperature for 2 days. Saturated NaCl (220 µL) was added. The mixture was shaken for 30 minutes and then the mixture was poured slowly into ethanol (30 mL). The mixture was allowed to stir slowly for 2 hours, and was then filtered. The solid was washed with ethanol and transferred it to a glass vial. The ethanol was evaporated and a resulting white fluffy material (51 mg) was dissolved in phosphate-NaCl buffer (4 mL) and shaken for 4 hours. 110 µL of a saturated NaCl was added and the mixture was shaken for 5 minutes and poured slowly onto 15 mL of ethanol. The mixture was left overnight and the white powder was filtered off and washed several times with EtOH and dried in vacuo. Yield 37 mg.

To show that the product contained dexamethasone attached to the hyaluronic hemi-ester, a sample was swollen in DMF (a few drops). Acetonitrile (1 mL) was added and after standing for 15 min LCMS was run on the acetonitrile solution. No dexamethasone was detected. To the gel slurry 20% NaOH (20 µL) was added and the slurry was shaken for 15 min at room temperature. The LCMS analysis was repeated and a peak corresponding to dexamethasone m/z 393 was detected.

Example 13

Pharmacokinetic Study of HSE-Diclofenac in Horses

Six healthy horses were injected in either the fetlock joint or in carpus with sterile solutions of diclofenac-succinyl-hyaluronan 10 mg/mL (2 mL). The horses were checked for adverse reactions such as swelling, heat evolution, and a motion analysis was performed. The motion analysis was independent of the investigator and performed with the help of sensors placed on the horse, measuring the symmetry of the motion of the horse. Synovial fluid was collected at certain time intervals and analyzed for free diclofenac and diclofenac linked to the succinate hyaluronan. A comparison was done with the injection of diclofenac (1 mg) mixed with a 0.5% hyaluronan (2 mL) solution.

The clinical investigation of the horses did not reveal any sign of adverse effects such as heat evolution or swelling. The motion analysis did not show any signs of limping. A pathological investigation of one of the horses did not show any macroscopic changes in the joints (fetlock or carpus).

The FIGURE shows the amounts of diclofenac analyzed after the injection of a solution of diclofenac linked to hyaluronan, SYN321, (prepared in accordance with Examples 5 and 7) compared to a hyaluronan-diclofenac mixture.

Example 14

Pharmacokinetic Study of HSE-Dexamethasone in Rabbit Eye 20 rabbits are subjected to cataract surgery with lens extraction. After removal of excess of Healon® GV used during the surgery, 50 µL of a HSE-dexamethasone conjugate solution (1% in physiological saline) is placed in the anterior chamber and left there. After 30 min, 2 h, 8 h, 32 and 128 h, intraoccular pressure is measured and samples are taken for the determination of the concentration of dexamethasone in the aqueous humor.

Example 15

Stability of a Sterilized Sample of HSE-Dexamethasone

HSE-dexamethasone (5 mg) was dissolved in physiological sodium chloride phosphate buffer pH 7.4 (0.5 mL) and the mixture was shaken overnight to a homogeneous viscous solution. 20 µL of the solution was removed and diluted with acetonitrile (200 µL). The mixture was shaken for 5 minutes and LC-MS was run. Dexamethasone could not be detected. The rest of the HSE-dexamethasone solution was heated for 15 minutes at 121° C. and 20 µL was removed and diluted with of acetonitrile (200 µL). LC-MS was run and dexamethasone could not be detected. 200 µL of the sterilized sample was removed and 20 µL of a 2N NaOH was added. The reaction mixture was stirred for 5 minutes and 20 µL of the sample was removed and diluted with 200 µL acetonitrile. LC-MS was run and dexamethsone could be detected.

Example 16

Hyaluronan Gel

Sodium hyaluronate (1000 mg) is stirred in 0.25 M NaOH (7.5 mL) until a viscous, homogeneous solution is obtained. Butandioldiglycidylether (63 µL) is added and the mixture is stirred with a teflon rod for a few minutes. The solution is heated at 50° C. for 2 h. The gel which formed is transferred to a beaker with water (10 L) and acetic acid (6 mL) The gel is collected from the medium using a fine net, and transferred to a 0.9% NaCl phosphate buffer pH 7.4 (2 L) and was allowed to stand at RT for 1 h. The gel is filtered off and new buffer solution (2 L) is added. The gel buffer mixture is heated at 95° C. overnight. The gel is collected on a net. As much as possible of the buffer is drained from the gel. A loose, soft gel is obtained.

The hyaluronan gel thus obtained can be dried by precipitation in ethanol. The precipitated material can be further dried in vacuum to obtain a solid material suitable for the linking of pharmaceuticals as described in the following Examples 17-19.

Example 17

Succinylated Hyaluronan Gel

The gel material from Example 16 (625 mg) is agitated in formamide (625 mL), pyridine (1.25 mL), and 4-(dimetylamino)-pyridine (15 mg), succinic anhydride (1.6 g) is added, and the slurry is stirred for 24 h at room temperature. The reaction mixture is poured into water (500 mL), and is occasionally shaken for 10 min. The gel-material is collected on a net, and is poured into another portion of water (500 mL). The washing procedure is repeated twice and the last wash is prolonged for 18 h. The gel material is collected on a net and dried by pouring it into ethanol (500 mL) and leaving it for 5 h, followed by washing the product in acetone overnight, followed by drying in vacuum. This procedure will typically give ~500 mg of succinylated hyaluronan gel-material in dried form.

Example 18

Hyaluronan Gel-Diclofenac Conjugate

The succinylated crosslinked gel-material from Example 17 (500 mg) is swollen in DMF containing water 25% (50 mL). N-methyl-morpholine (83 µL), HOBT (1.3 mg) and a DMF solution of 2-(2,6-Dichloro-phenylamino)-phenyl]-acetic acid 2-(2-amino-ethoxy)-ethyl ester 397 mg/mL (116 µL, 46 mg) is added to the stirred succinyl-hyaluronan solution. The reaction is agitated vigorously for a few minutes. EDC (15 mg) is added and the agitation is continued for 18 hours at room temperature. The washing procedure from Example 17 typically gives the diclofenac-substituted hyaluronan gel-material, ~400 mg when dried.

Example 19

The diclofenac-substituted hyaluronan gel-material, from Example 18, (250 mg) is swollen in physiological saline (12.5 mL) over night. A swollen gel is obtained that can be loaded into syringes, and heat sterilized. Optionally the gel can be swollen in a solution of hyaluronan in a physiological saline solution, and can be heat sterilized. This procedure adds the possibility to further control the rheological properties of the final product.

The examples and specific embodiments described herein are illustrative only and are not to be construed as limiting the scope of the invention defined by the appended claims.

REFERENCES

1. L Stefan Lohmander, Nils Dalen, Gunnar Englund, Martti Hamalainen, Erik Martin Jensen, Kerstin Karlsson, Magnus Odensten, Leif Ryd, Ingemar Sembo, Olavi Suomalainen, Agnar Tegnander, *Intra-articular hyaluronan injections in the treatment of osteoarthritis of the knee: a randomised, double blind, placebo controlled multicentre trial*. Annals of the Rheumatic Diseases 1996; 55: 424-431

2. Anette Jørgensen, Kristian Stengaard-Pedersen, Ole Simonsen, Mogens Pfeiffer-Jensen, Christian Eriksen, Henning Bliddal, Niels Wisbech Pedersen, Søren Bødtker, Kim Horslev-Petersen, Lennart ØSnerum, Niels Egund, Helle Frimer-Larse *Intra-articular hyaluronan is without clinical effect in knee osteoarthritis: a multicentre, randomised, placebo-controlled, double-blind study of 337 patients followed for 1 year*. Annals of the Rheumatic Diseases 2010; 69:1097-1102

3. Jasmin Arrich, Franz Piribauer, Philipp Mad, Daniela Schmid, Klaus Klaushofer, Marcus Müllner *Intra-articular hyaluronic acid for the treatment of osteoarthritis of the knee: systematic review and meta-analysis*. CMAJ•Apr. 12, 2005; 172 (8)

4. Torvard C. Laurent, Krister Hellsing, Bertil Gelotte *Crosslinked Gels of Hyaluronic Acid*. Acta. Chem. Scand. 18 (1964) No. 1

5. Tomas Mälson and Bengt Lindqvist Gel of crosslinked hyaluronic acid for use as a vitreous substitute. U.S. Pat. No. 4,716,154, Dec. 29, 1987

6. Kenji Miyamoto, Yousuke Yasuda and Keniji Yoshioka Patent application US 2011/0083991 A1

7. Kristiina Kyyrönen, Lisbeth Hume, Luca Benedetti, Arto Urtti, Elisabeth Topp, Valentino Stella *Methylprednisolone esters of hyaluronic acid in ophthalmic drug delivery*. International Journal of Pharmaceutics, vol. 80, 1992, 161-69

8. Joseph Price Remington *The Science and Practice of Pharmacy*, Lippincott Williams & Wilkins, 2006, page 780

The invention claimed is:

1. A method for manufacturing a hyaluronan conjugate, comprising reacting hyaluronan in solution or gel form with an anhydride reagent to provide a hyaluronan hemi-ester, and subsequently binding the hyaluronan hemi-ester to a pharmaceutically active compound to form a hyaluronan conjugate having free hemi-ester groups, the pharmaceutically active compound bound to the hyaluronan via hemi-ester groups, and free OH groups, wherein the hyaluronan conjugate has the structure:

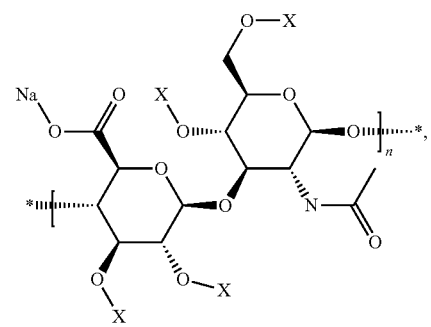

wherein each instance of X in the hyaluronan conjugate is independently
H,
—CO—$CH_2CH_2$—COONa,
—CO—$CH_2CH_2$—CO—NH—$CH_2CH_2$—O—$CH_2CH_2$—O-DRUG, or
—CO—$CH_2CH_2$—CO—NH—$CH_2CH_2$—O—$CH_2CH_2$—O—CO—$CH_2CH_2$—CO-DRUG,
wherein DRUG represents the pharmaceutically active compound.

2. The method according to claim 1, wherein the hyaluronan in solution or gel form is the product of a process comprising dissolving hyaluronan in formamide with the addition of a tertiary amine, and wherein the anhydride reagent is succinic anhydride.

3. The method according to claim 1, wherein the pharmaceutically active compound is diclofenac or dexamethasone.

4. A hyaluronan conjugate comprising hyaluronan having free hemi-ester-groups, a pharmaceutically active compound bound to the hyaluronan via hemi-ester groups, and free OH groups, wherein the hyaluronan conjugate has the structure:

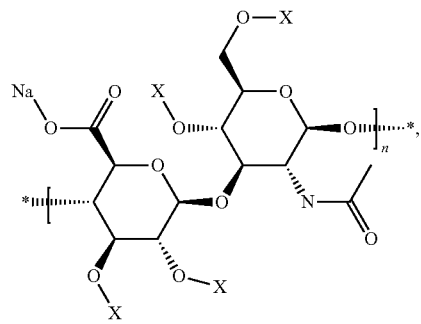

wherein each instance of X in the hyaluronan conjugate is independently
H,
—CO—$CH_2CH_2$—COONa,
—CO—$CH_2CH_2$—CO—NH—$CH_2CH_2$—O—$CH_2CH_2$—O-DRUG, or
—CO—$CH_2CH_2$—CO—NH—$CH_2CH_2$—O—$CH_2CH_2$—O—CO—$CH_2CH_2$—CO-DRUG,
wherein DRUG represents the pharmaceutically active compound.

5. The hyaluronan conjugate according to claim 4, wherein the pharmaceutically active compound is diclofenac or dexamethasone.

6. The hyaluronan conjugate according to claim 4, wherein the hyaluronan is crosslinked.

7. The hyaluronan conjugate according to claim 4, wherein the substitution degree is from 0.01 to 0.3 mol of the pharmaceutically active compound per mol of hyaluronan disaccharide repeating unit.

8. The hyaluronan conjugate according to claim 4, wherein the pharmaceutically active compound is diclofenac.

9. A method of treating a joint disease in a human or veterinary patient, comprising administering an effective amount of the hyaluronan conjugate according to claim 4 to the patient.

10. A method of treating a joint disease according to claim 9, wherein the patient is a horse.

11. A method of treating a cataract in a human or veterinary patient, comprising administering an effective amount of the hyaluronan conjugate according to claim 4 to the patient.

12. A method of treating colon or lung cancer in a human or veterinary patient, comprising administering an effective amount of the hyaluronan conjugate according to claim 4 to the patient.

13. A composition comprising the hyaluronan conjugate according to claim 4, wherein the hyaluronan conjugate is heat sterilized and in a buffered physiological saline.

14. A composition comprising the hyaluronan conjugate according to claim 4, and hyaluronan having a molecular weight of about 100,000 to 4,000,000.

15. A composition comprising the hyaluronan conjugate according to claim 4, in the form of a gel matrix, dry film or dry particles.

16. The method of claim 12, wherein the pharmaceutically active compound is paclitaxel, docetaxel, doxorubicin or daunorubicin.

17. A method of delivering an anti-cancer drug to a human or veterinary patient, comprising administering the hyaluronan conjugate according to claim 4 to the patient, wherein the pharmaceutically active compound is an anti-cancer drug.

18. The method of claim 2, further comprising forming the hyaluronan in solution or gel form by dissolving hyaluronan in formamide with the addition of a tertiary amine.

* * * * *